US011577264B2

(12) United States Patent
Savalle

(10) Patent No.: US 11,577,264 B2
(45) Date of Patent: Feb. 14, 2023

(54) DEVICE FOR DISPENSING A FLUID PRODUCT

(71) Applicant: APTAR FRANCE SAS, Le Neubourg (FR)

(72) Inventor: Matthieu Savalle, Oissel (FR)

(73) Assignee: APTAR FRANCE SAS, Le Neubourg (FR)

(*) Notice: Subject to any disclaimer, the term of this patent is extended or adjusted under 35 U.S.C. 154(b) by 0 days.

(21) Appl. No.: 17/290,877

(22) PCT Filed: Nov. 8, 2019

(86) PCT No.: PCT/FR2019/052665
§ 371 (c)(1),
(2) Date: May 3, 2021

(87) PCT Pub. No.: WO2020/099766
PCT Pub. Date: May 22, 2020

(65) Prior Publication Data
US 2021/0387218 A1     Dec. 16, 2021

(30) Foreign Application Priority Data

Nov. 14, 2018    (FR) ...................................... 1860498

(51) Int. Cl.
    *B05B 11/00*       (2006.01)
    *A61M 11/00*      (2006.01)
    *A61M 15/00*      (2006.01)
(52) U.S. Cl.
    CPC ...... *B05B 11/3009* (2013.01); *B05B 11/3056* (2013.01); *B05B 11/3059* (2013.01); *A61M 11/007* (2014.02); *A61M 15/0071* (2014.02)

(58) Field of Classification Search
CPC ............. B05B 11/3009; B05B 11/3056; B05B 11/3059; B05B 11/025; A61M 11/007; A61M 15/0071
See application file for complete search history.

(56) References Cited

U.S. PATENT DOCUMENTS 6,419,124 B1 * 7/2002 Hennemann ........ B05B 11/3052
                                               222/162
6,626,379 B1 * 9/2003 Ritsche ............... B05B 11/0078
                                               239/303

(Continued)

FOREIGN PATENT DOCUMENTS

WO         2014/147329 A1     9/2014

OTHER PUBLICATIONS

International Search Report for PCT/FR2019/052665, dated Mar. 5, 2020.

(Continued)

*Primary Examiner* — Vishal Pancholi
(74) *Attorney, Agent, or Firm* — Sughrue Mion, PLLC

(57) ABSTRACT

A device for dispensing a fluid product having a container (10), a dispensing member (20), a dispensing head (30) with an outlet (31), an actuating member (60) slidably mounted in the dispensing head, and a lateral actuating system cooperating with the actuating member. The actuating member has a cylindrical body (65) and a flexible tab (61) having a radial projection (62), the flexible tab extending axially into the cylindrical body (65) and radially deformable between an undeformed position, in which the projection (62) projects radially out of the cylindrical body, and a deformed position, in which the projection does not. The lateral actuating system has two side levers (35, 36) diametrically opposed, deformable and/or movable laterally, a flexible spacer (37) connecting the two side levers, the flexible spacer cooperating with the projection (62) and (Continued)

Figure 1:
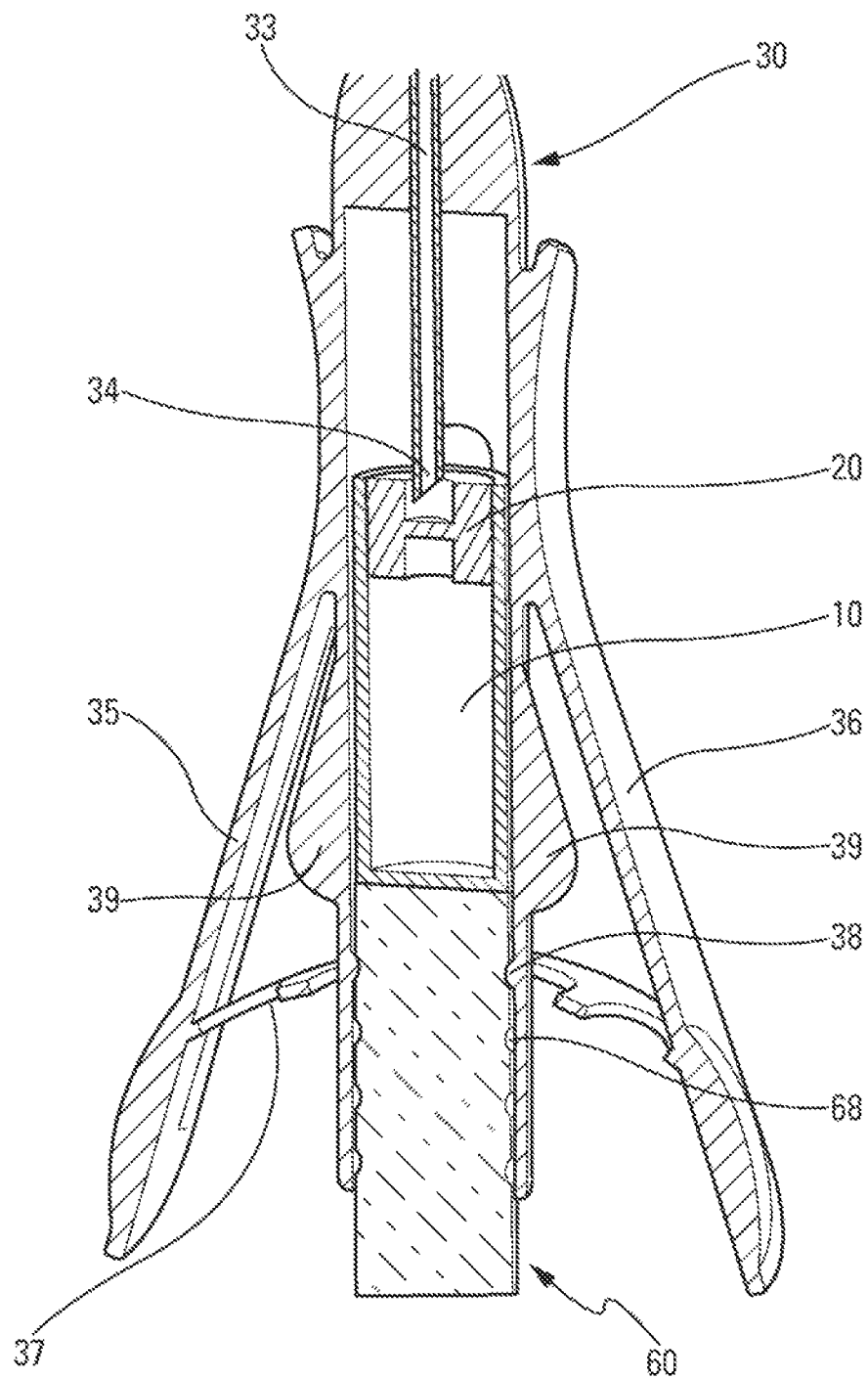

axially deformed during actuation to axially move the actuating member relative to the dispensing head.

13 Claims, 2 Drawing Sheets

(56) References Cited

U.S. PATENT DOCUMENTS

| | | | | |
|---|---|---|---|---|
| 7,306,129 | B2* | 12/2007 | Swiss | B65D 47/205 |
| | | | | 222/326 |
| 7,571,838 | B2* | 8/2009 | Wolter | B05B 11/02 |
| | | | | 222/391 |
| 10,232,127 | B2* | 3/2019 | Petit | A61M 5/31591 |
| 10,322,237 | B2* | 6/2019 | Fabien | A61M 5/2033 |
| 2004/0262339 | A1* | 12/2004 | Stradella | B05B 11/02 |
| | | | | 222/321.6 |
| 2005/0056664 | A1 | 3/2005 | Wolter et al. | |
| 2005/0284890 | A1* | 12/2005 | Heldt | B65D 83/0033 |
| | | | | 222/321.7 |
| 2007/0131721 | A1 | 6/2007 | Fritschi et al. | |
| 2014/0290652 | A1 | 10/2014 | Davies et al. | |

OTHER PUBLICATIONS

Written Opinion of the International Searching Authority dated Mar. 5, 2020 in Application No. PCT/FR2019/052665.

\* cited by examiner

DEVICE FOR DISPENSING A FLUID PRODUCT

CROSS REFERENCE TO RELATED APPLICATIONS

This application is a National Stage of International Application No. PCT/FR2019/052665 filed Nov. 8, 2019, claiming priority based on French Patent Application No. 1860498 filed Nov. 14, 2018.

The present invention relates to a fluid product dispensing device, or more particularly, to a bidose-type device.

A "bidose type dispensing device" means a device containing two doses of fluid product to be dispensed during two successive actuations of the dispensing device.

Bidose type devices are well known in the prior art. These devices generally comprise a container containing two doses of fluid product to be dispensed and a dispensing member, which is generally a piston, slidably mounted in said container and moved to dispense the fluid product contained in said container. When the device is of the bidose type, the piston is moved in two successive actuating strokes so that a first dose is dispensed during a first actuation and a second dose is dispensed during a second actuation.

Devices of this type may have drawbacks.

Thus, in the case of a nasal device where actuation is in the axial direction, the axial actuation force applied to the device by the user during actuation may cause the device to axially move in the user's nostril which may cause discomfort or even risk of injury.

Besides, devices containing few doses, such as bidoses, may pose the risk of partial or incomplete distribution, depending on the actuating force applied to the device by the user.

Another drawback encountered with devices such as bidoses is the sequence of actuation to dispense the doses, usually requiring the use of both hands to dispense the two doses in succession.

Furthermore, with this type of device, especially of the bidose type, it is sometimes difficult for the user to know if he has dispensed one or more doses with his device. However, depending on the type of fluid product that is dispensed by the device, especially in the case of a medical product, it may be important to avoid any risk of under- and/or overdose. Thus, for example, if the bidose type device is intended to dispense a respective dose to each nostril, it is usually undesirable for both doses to be dispensed in the same nostril. However, a user who would have used the device to dispense a first dose into the first nostril, and then put it down or would become distracted, may, if unsure of having used the device once, dispense the second dose into the same nostril as the first dose. This is generally not desirable. Thus, if the product is expelled twice in the same nostril, the exceeding active substance will not be properly absorbed by the tissues or immediately leak out of the nostril with an obvious loss of effectiveness. Besides, no dose will be available for the second nostril.

Also, the number of parts and assembly steps for this type of devices can result in high manufacturing and assembly costs.

US2007131721, US2005056664 and US2014290652 describe devices of the prior art.

The present invention aims to create a device for dispensing a fluid product which does not reproduce the aforementioned drawbacks.

The present invention also aims to create such a device for dispensing a fluid product that avoids any risk of injury during actuation.

The present invention also aims to create such a device for dispensing a fluid product that guarantees to dispense a full dose each time the device is actuated.

The present invention also aims to create a device for dispensing a fluid product that reliably indicates to the user the number of doses dispensed.

The present invention also aims to provide such a device for dispensing a fluid product that is simple and inexpensive to manufacture and assemble.

Thus, the present invention relates to a device for dispensing a fluid product comprising a container containing at least one dose of fluid product, a dispensing member, such as a piston, which is slidably mounted in said container to dispense fluid product, a dispensing head provided with a dispensing outlet, said container being movable relative to said dispensing head to move said dispensing member into said container and thus dispense fluid product through said dispensing outlet, an actuating member which is slidably mounted in said dispensing head and cooperates with said container, and a lateral actuating system which cooperates with said actuating member, wherein:

said actuating member comprises a cylindrical body and at least one flexible tab provided with at least one radial projection, each flexible tab extending axially in said cylindrical body and being radially deformable between an undeformed position, in which said at least one radial projection projects radially out of said cylindrical body, and a deformed position, in which said at least one radial projection does not project radially out of said cylindrical body, said lateral actuating system comprises two side levers which are diametrically opposed, deformable and/or laterally movable relative to said dispensing head, at least one flexible spacer connecting said two side levers, said at least one flexible spacer cooperating with a radial projection of said actuating member and being axially deformed during actuation in order to move said actuating member axially relative to said dispensing head.

Advantageously, said actuating member comprises two radially flexible tabs, which are diametrically opposed.

Advantageously, said container contains two doses of fluid product, dispensed during two successive actuations of the device.

Advantageously, each radially flexible tab of said actuating member comprises two axially offset radial projections for dispensing two successive doses.

Advantageously, said side levers are each formed by a flexible elongated blade, one end of which, proximal to the dispensing outlet, is attached to said dispensing head, and the opposite end of which, distal from the dispensing outlet, is radially spaced from said dispensing head, said at least one flexible spacer being dome shaped and connecting said two flexible elongated blades in the vicinity of said distal ends.

Advantageously, said side levers are deformable and/or laterally movable, between a rest position in which they are distant from said dispensing head, and an actuating position in which they are close to said dispensing head, the movement of said side levers towards the actuating position deforming and/or compressing said at least one flexible spacer by increasing its curvature, and thus axially moving the apex of the curvature towards the dispensing outlet.

Advantageously, stops are provided on the dispensing head to define the actuating position of said side levers.

Advantageously, before the first actuation, all the radial projections are arranged axially behind the apex of the curvature of said at least one flexible spacer to form an actuation safety feature which prevents accidental actuation of the device.

Advantageously, to activate the device, the activating member is moved axially relative to said dispensing head until said at least one flexible spacer is positioned below the first radial projection of said activating member.

Advantageously, said device comprises an indicator to indicate to the user the dispensing of each dose.

Advantageously, said indicator comprises viewing windows formed in said dispensing head.

Advantageously, said actuating member comprises radial notches cooperating with radial projections of said dispensing head, to maintain the actuating member in position in said dispensing head before and after actuation.

Figure 2:
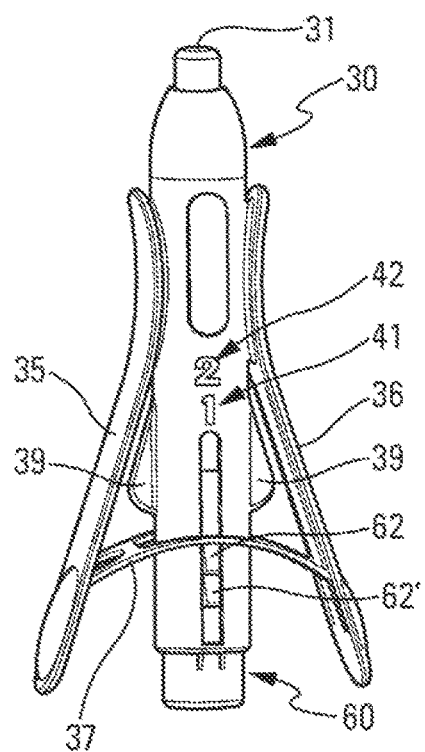
Figure 3:
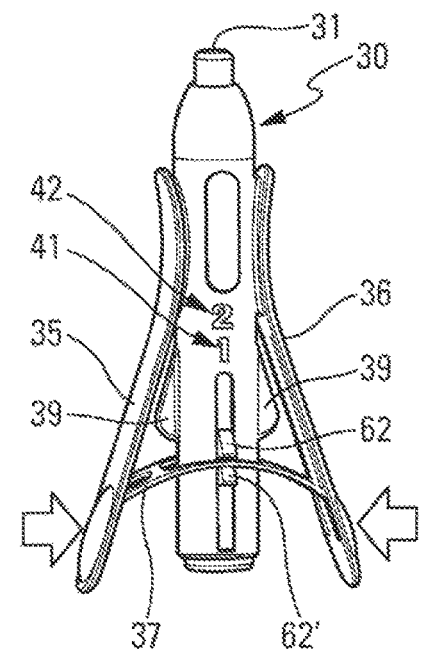
Figure 4:
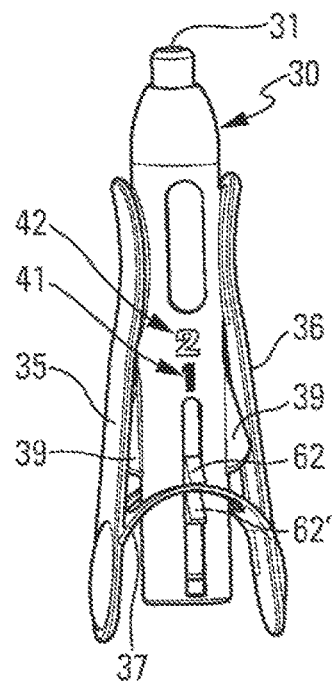
Figure 5:
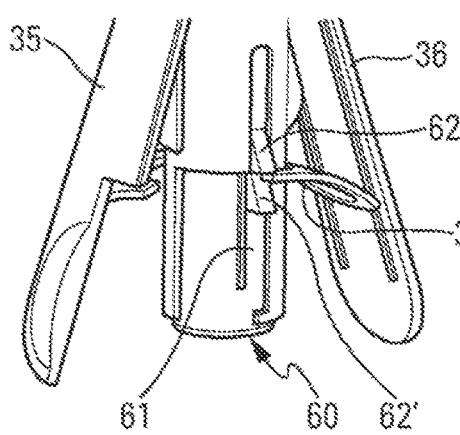
Figure 6:
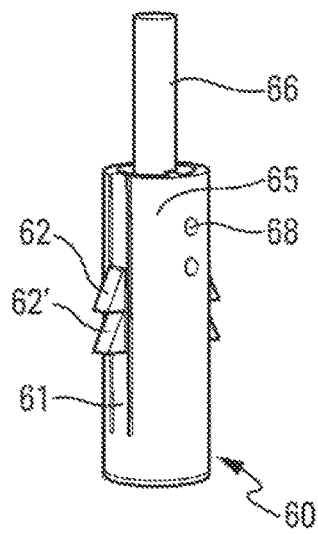

These and other advantages and features of the present invention will become clearer with the following detailed description, made with reference to the attached drawings given as non-limiting examples, and wherein:

FIG. 1 is a partial schematic perspective cutaway view of a device for dispensing a fluid product according to an advantageous embodiment, FIGS. 2, 3 and 4 are schematic perspective views of a device for dispensing a fluid product according to an advantageous embodiment, respectively before unlocking, before dispensing of the first dose, and after dispensing of the first dose, FIG. 5 is an enlarged, partially cut-out detail view of the device in FIG. 3, FIG. 6 is a schematic perspective view of the actuating member of FIGS. 1 to 5, and FIG. 7 is similar to FIG. 6, showing another alternative embodiment of the actuating member.

Figure 7:
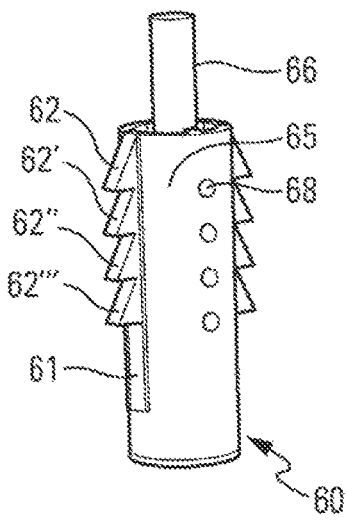

The present invention will be mainly described hereinafter concerning an exemplary embodiment which is a bidose, i.e., a device containing two doses of fluid product to be dispensed upon two successive actuations of the device. However, it must be understood that the present invention could be applied to devices having any number of doses, for example four doses as shown in the alternative of FIGS. 1 and 7. Likewise, the bidose type device shown in FIGS. 2 to 6 is only one possible exemplary embodiment to which the present invention applies, and it must be understood that the present invention applies more generally to any type of device containing at least two doses.

Referring to FIGS. 1 to 4, the dispensing device comprises a container 10 containing two doses of fluid product. A dispensing member 20, such as a piston, is slidably mounted in said container, in a known manner. Before the device is actuated, the piston acts as a plug, isolating the contents of the container. Document WO2014147329 describes, in particular, such a container provided with such a piston.

The container is mounted in a dispensing head 30 being axially movable relative thereto. In particular, an axial movement of the container 10 relative to the dispensing head 30 causes the piston 20 to move in the container and thus the dispensing of the fluid product contained in said container. The dispensing head 30 comprises a dispensing outlet 31 and a dispensing channel 33 leading from a piercing tip 34 to this dispensing outlet 31.

A spray profile, which may be of any known type and not shown in more detail in the drawings, can be provided upstream of the dispensing outlet 31 for dispensing liquid product in spray form.

In the example shown, the container 10 is directly attached into the dispensing head 30. Alternatively, the container 10 could be attached in a body, which would thus be integral with said container 10, and which would move together with it.

The dispensing head 30 comprises a lateral actuating system adapted to cooperate with an actuating member 60.

Said actuating member 60 is mounted in the dispensing head 30, being movable in the axial direction, to perform one or more sequential actuations of the device. This actuating member 60 comprises a cylindrical body 65 and at least one flexible tab 61 provided with at least one radial projection 62. Each flexible tab axially extends into said cylindrical body 65 and is radially deformable between an undeformed position in which said at least one radial projection 62 projects radially out of said cylindrical body 65, and a deformed position in which said at least one radial projection 62 is moved radially inwardly of said cylindrical body 65 so that it no longer projects radially out of said cylindrical body 65.

Advantageously, the actuating member 60 comprises radial notches 68, preferably rounded, cooperating with radial projections 38, preferably rounded, of the dispensing head 30, to maintain the actuating member 60 in position in said dispensing head 30 before and after actuation.

In the examples of FIGS. 6 and 7, there are two radially flexible tabs 61, which are diametrically opposed.

In the example of FIG. 6, there are two radial projections 62, 62', axially offset on each radially flexible tab 61 to dispense two successive doses.

In the example shown in FIG. 7, there are four radial projections 62, 62', 62", 62''' axially offset on each radially flexible tab 61 to dispense four successive doses. Any number of radial projections is possible.

Said actuating member 60 may further comprise an axial rod 66, adapted upon actuation to cooperate with the container 10 or with the body supporting said container, to move it axially relative to the dispensing head 30.

The lateral actuating system comprises two diametrically opposed side levers 35, 36, which are deformable and/or laterally movable relative to the dispensing head 30.

In the example of the Figures, each of these side levers is formed by a flexible elongated blade, a proximal end of the dispensing outlet 31 being attached to the dispensing head 30 and the opposite end, distal from the dispensing head 31, being radially spaced from the dispensing head 30.

At least one flexible spacer 37 connects said two flexible elongated blades, preferably in the vicinity of said distal ends.

Advantageously, each flexible spacer 37 is in dome shaped in the direction of the dispensing outlet 31, as seen in FIGS. 1 to 5.

If the actuating member 60 comprises two radially flexible tabs 61, which are diametrically opposed, as in the examples of the Figures, then there are two flexible spacers 37, extending on either side of said actuating member 60. Advantageously, a single flexible spacer 37 may be provided, with two tabs, one on each side of said actuating member 60.

The side levers 35, 36 are deformable and/or laterally movable, thus approximately radially, between a rest position visible in FIG. 3 and an actuated position visible in FIG. 4, in which the two side levers are brought closer to said dispensing head 30, thereby compressing the flexible spacers 37 by increasing their curvature, and thus axially moving the apex of the curvature toward the dispensing outlet 31.

Advantageously, stops 39 are provided on the dispensing head 30 to define the actuating position of the side levers.

Upon actuation, each flexible spacer 37 cooperates, via its apex of curvature, with a radial projection 62 of said actuating member 60 to generate an axial movement of said actuating member 60.

The operation of the device shown in FIGS. 2 to 4 is as follows.

Advantageously, an actuation safety feature is provided to prevent accidental actuation of the device. In the example shown, in the starting position in FIG. 2, all radial projections 62, 62' are axially located behind the apex of the curvature of the flexible spacer 37. Thus, if the side levers are moved or deformed to their actuating position, the flexible struts' compression will not affect the actuating member 60.

Before actuation, the user must therefore activate the device by axially moving the activating member 60 relative to the dispensing head 30, for example by pressing on the bottom of said actuating member 60 until the flexible spacer 37 comes to be positioned under the first radial projection 62, as seen in FIG. 3.

Advantageously, the flexible tabs 61 are radially deformed inwardly to allow said flexible spacer 37 to pass over the first radial projection 62.

The device is now ready for actuation.

When the user simultaneously presses the two side levers 35, 36, to bring them closer to the dispensing head 30, he will therefore deform, in particular compress, the flexible spacer 37. The latter will therefore have its apex of curvature axially moved towards the dispensing outlet 31. Being arranged under the first radial projection 62, this axial movement of the flexible spacer 37 causes the axial movement of the actuating member 60.

This will move the container 10 relative to the dispensing head 30. In the initial position shown in FIG. 2, the piston 20 isolates the contents of the container 10 from the atmosphere. As the container 10 begins to move relative to the dispensing head 30, the piercing end 34 of the dispensing channel 33 will pierce the piston 20 to provide communication between the interior of the container 10 and said dispensing outlet 31. Further actuation will cause the piston 20 to move within the container 10 and thus a dispensing of the first dose. The fluid product is therefore pushed by said piston 20 through the piercing end 34 into the dispensing channel 33 and then via the spray profile out of the device through the dispensing outlet 31.

After the first dose has been dispensed, the device is in the position shown in FIG. 4, and when the user releases its pressure on the side levers 35, 36, the compressed flexible spacer 37 and/or the elasticity of said levers returns them to their rest position. The flexible spacer 37 then pushes on the next radial projection 62' of the activating member, thus causing the radial deformation of the flexible tab 61, and thus allowing the flexible spacer 37 to come into position under the next radial projection 62'.

The second or others doses are then dispensed in the same way as described above, by repeating the same actuation cycle.

The dispensing device comprises an indicator to indicate to the user that the first dose is dispensed and that the second dose is dispensed. In this way, the user exactly knows the situation and whether the first dose has been dispensed. This indicator comprises viewing windows 41, 42 formed in said dispensing head 30. Advantageously, these viewing windows are formed in the head's side wall, clearly visible to the user when holding the device in the hand. Of course, if the number of doses of fluid product contained in the container is different from two, then the number of viewing windows will also be different from two. These viewing windows can in particular be made in the form of holes in the wall of the dispensing head 30, as shown in Figures.

Advantageously, the axial rod 66 of the actuating member 60 becomes visible in the first viewing window 41 after the first dose has been dispensed and in the second viewing window 42 after the second dose has been dispensed. Advantageously, said axial rod 66 of the actuating member 60 is made in a color that is clearly visible to the user, for example in red.

The device of the invention thus has many advantages, including:
- simple and straightforward to use;
- ergonomic side actuation;
- no user action required between doses;
- dose indicator;
- user-independent device performance;
- symmetrical design and shape;
- declination in any number of doses;
- limited number of components.

The present invention has been described concerning alternative embodiments which are however not limiting, and any useful modifications may be made to the present invention within the scope defined by the appended claims.

The invention claimed is:

1. A device for dispensing a fluid product comprising a container containing at least one dose of fluid product, a dispensing member, a dispensing head provided with a dispensing outlet, said container being movable relative to said dispensing head to move said dispensing member in said container and thus dispense fluid product through said dispensing outlet, an actuating member which is slidably mounted in said dispensing head and cooperates with said container, and a lateral actuating system which cooperates with said actuating member, characterized in that:

said actuating member comprises a cylindrical body and at least one flexible tab provided with at least one radial projection, each flexible tab axially extending in said cylindrical body and being radially deformable between an undeformed position, in which said at least one radial projection radially projects out of said cylindrical body, and a deformed position, in which said at least one radial projection does not radially project out of said cylindrical body, said lateral actuating system comprises two side levers which are diametrically opposed, deformable and/or laterally movable relative to said dispensing head, at least one flexible spacer connecting said two side levers, said at least one flexible spacer cooperating with a radial projection of said actuating member and being axially deformed upon actuation to move said actuating member axially with respect to said dispensing head.

2. The device according to claim 1, wherein said actuating member comprises two radially flexible tabs which are diametrically opposed.

3. The device according to claim 1, wherein said container contains two doses of fluid product, dispensed during two successive actuations of the device.

4. The device according to claim 3, wherein each radially flexible tab of said actuating member comprises two axially offset radial projections for dispensing two successive doses.

5. The device according to claim 1, wherein said side levers are each formed by a flexible elongated blade, one end of which, proximal to the dispensing outlet, is attached to the said dispensing head, and the opposite end of which, distal from the dispensing outlet, is radially spaced from the said dispensing head, said at least one flexible spacer being dome shaped and connecting said two flexible elongated blades in the vicinity of the said distal ends.

6. The device according to claim 5, wherein said side levers are deformable and/or laterally movable, between a rest position in which they are distant from said dispensing head, and an actuating position in which they are close to said dispensing head, the movement of said side levers towards the actuating position deforming and/or compressing said at least one flexible spacer by increasing its curvature, and thus axially moving the apex of the curvature towards the dispensing outlet.

7. The device according to claim 5, wherein stops are provided on the dispensing head to define the actuating position of said side levers.

8. The device according to claim 1, wherein before the first actuation, all radial projections are axially arranged behind the apex of the curvature of said at least one flexible spacer to form an actuation safety feature which prevents accidental actuation of the device.

9. The device according to claim 8, wherein to activate the device, the activating member is axially moved relative to said dispensing head until said at least one flexible spacer is positioned below the first radial projection of said activating member.

10. The device according to claim 1, comprising an indicator for indicating to the user the dispensing of each dose.

11. The device according to claim 10, wherein said indicator comprises viewing windows formed in said dispensing head.

12. The device according to claim 1, wherein said actuating member comprises radial notches cooperating with radial projections of said dispensing head, to maintain the actuating member in position in said dispensing head before and after actuation.

13. The device according to claim 1, wherein the dispensing member is a piston that is slidably mounted in the container to dispense fluid product.

* * * * *